US00PP15875P2

(12) United States Plant Patent
Olesen et al.

(10) Patent No.: US PP15,875 P2
(45) Date of Patent: Jul. 19, 2005

(54) FLORIBUNDA ROSE PLANT NAMED 'POULCS009'

(50) Latin Name: *Rosa hybrid*
Varietal Denomination: POULcs009

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 40 days.

(21) Appl. No.: 10/812,708

(22) Filed: Mar. 29, 2004

(51) Int. Cl.[7] ..... A01H 5/00
(52) U.S. Cl. ..... Plt./149
(58) Field of Search ..... Plt./149, 148, 150

*Primary Examiner*—Anne Marie Grunberg
*Assistant Examiner*—June Hwu

(57) ABSTRACT

A new garden rose plant of the floribunda class which has abundant, pink flowers and attractive foliage. This new and distinct variety has shown to be uniform and stable in the resulting generations from asexual propagation.

2 Drawing Sheets

Botanical classification: *Rosa* hybrid.
Variety denomination: 'POULcs009'.

SUMMARY OF THE INVENTION

The present invention constitutes a new and distinct variety of garden rose plant which originated from a controlled crossing between the female parent 'POULdrik' described and illustrated in U.S. Plant Pat. No. 12,557 issued on Apr. 23, 2002, and the male parent an unnamed seedling. The two parents were crossed during the summer of 1994 and the resulting seeds were planted in a controlled environment in Fredensborg, Denmark. The new variety is named 'POULcs009'.

The new variety may be distinguished from its female seed parent, 'POULdrik' by the following combination of characteristics:

1. While the seed parent 'POULdrik' has a flower color of Red Group 52C the same of 'POULcs009' is Red-Purple Group 65D with intonations of Red-Purple Group 64D.
2. While the seed parent 'POULdrik' has 14 to 18 petals, 'POULcs009' has 50.
3. While the seed parent 'POULdrik' has a flower diameter of 60 mm, the same of 'POULcs009' is 50 mm.

The new variety may be distinguished from its unnamed male pollen parent by the following combination of characteristics:

1. The pollen parent has very pale pink flowers, while 'POULcs009' has medium pink flowers.
2. The pollen parent a low growth habit, ranging from 40 to 60 cm, while 'POULcs009' has an average height of 76 cm.
3. Flowers of 'POULcs009' have a longer lasting quality on the plant than those of the pollen parent.

The objective of the hybridization of this rose variety was to create a new and distinct variety for garden use with unique qualities, such as:

1. Uniform and abundant pink flowers;
2. Vigorous, but compact and even growth when propagated both as a budded rose and on its own roots;
3. Disease resistance;

4. Flower color which does not fade;
5. Well suited to normal cultural practices in the garden and in containers.

This combination of qualities is not present in previously available commercial cultivars of this type, known to the inventors, and distinguish 'POULcs009' from all other varieties of which we are aware.

As part of their rose development program, L. Pernille Olesen and Mogens N. Olesen germinated the seeds from the aforementioned hybridization during winter of 1994 and conducted evaluations on the resulting seedlings in a controlled environment in Fredensborg, Denmark.

'POULcs009' was selected in the spring 1995 by the inventors as a single plant from the progeny of the aforementioned hybridization.

Asexual reproduction of 'POULcs009' by traditional budding and rooted cuttings was first done by L. Pernille and Mogens N. Olesen in their nursery in Fredensborg, Denmark in July, 1995. This initial and other subsequent asexual propagations conducted in controlled environments have demonstrated that the characteristics of 'POULcs009' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULcs009'. Specifically illustrated in the drawing: SHEET 1:

FIG. 1.1; Open flower, stem showing open flower, branching, and

FIG. 1.2; Flower bud closed, flower bud as sepals unfold, and partially open;

FIG. 1.3; Flower petals, detached;

Specifically illustrated in SHEET 2:

FIG. 2.1; Sepals, receptacle, and peduncle;

FIG. 2.2; Leaves;

FIG. 2.3; Bare stems.

DETAILED DESCRIPTION OF THE VARIETY

The following is a description of 'POULcs009', as observed in its growth in a field nursery in Jackson County, Oreg. Observed plants are 3 years of age. Color references are made using The Royal Horticultural Society (London, England) Colour Chart, 1995, except where common terms of color are used.

For a comparison, several physical characteristics of the rose variety, 'POULfl002', a rose variety from the same inventors described and illustrated in U.S. Plant patent application Ser. No. 10/685,543 dated Oct. 14, 2003 are compared to 'POULcs009' in Chart 1.

CHART 1

| | POULcs009 | POULf1002 |
|---|---|---|
| General Tonality of Open Flower | Red-Purple Group 62C | Red Group 52 D |
| Peduncle Length | 35 to 40 mm | 40 to 50 mm |
| Petalage | 50 petals | 20 to 25 petals |

FLOWER AND FLOWER BUD

Blooming habit: Continuous.

Flower bud:

*Size.*—Upon opening, 25 mm in length from base of receptacle to end of bud.

*Bud form.*—Broad-based ovoid.

*Bud color.*—As sepals unfold, petals are Red-Purple Group 58D. At ¼ opening petals are Red-Purple Group 58D with intonations of Red-Purple Group 58A.

*Sepals.*—Upper Surface: Color: Yellow-Green Group 146B. Texture: Moderately pubescent. Lower Surface: Color: Yellow-Green Group 146B. Sepal Shape: Sepal apex is cirrhose. Base is flat at union with receptacle. Sepal Margin: Stipitate glands are in medium quantity at margins and lower surfaces. Size: 23 mm (l)×7 mm (w).

*Receptacle.*—Surface Texture: Smooth. Shape: Funnel shaped. Size: 9 mm (h)×6 mm (w). Color: Yellow-Green Group 144A.

*Peduncle.*—Surface: Smooth. Length: 40 to 70 mm average length. Diameter: 3.5 mm. Color: Yellow-Green Group 144B. Anthocyanic pigments the color of Greyed-Red Group 178A observed.

*Borne.*—In clusters of 5 flower buds per stem.

*Pedicel.*—Length: 35 to 40 mm. Diameter: 3 mm. Strength: Strong. Texture: Somewhat rough due to the presence of stipitate glands.

Flower bloom:

*Fragrance.*—Light floral scent.

*Duration.*—The blooms have a duration on the plant of approximately 10 to 14 days. Afterwards, petals fall cleanly away from plant.

*Size.*—Flower diameter is 50 mm when fully open. Flower depth is 35 mm.

*Form.*—Flowers resemble an open cup, with strongly reflexed petals which curve outward from the center.

*Shape of flower when viewed from the side.*—Upon opening, upper part: Flat. Upon opening, lower part: Flattened Convex. Open flower, upper part: Flat. Open flower, lower part: Flattened Convex.

*Petalage.*—50 petals on average with 5 to 10 petaloids.

Color:

*Upon opening, petals.*—Outermost petals: Outer side: Red-Purple Group 63D with marginal intonations of Red-Purple Group 64B to 64C. Inner Side: Red-Purple Group 63C to Red-Purple Group 58D.

*Innermost petals.*—Outer side: Red-Purple Group 63D with marginal intonations of Red-Purple Group 64C. Inner Side: Red-Purple Group 63C.

*Upon opening, basal petal spots.*—Outermost petals: Outer side: Yellow Group 4C. Inner Side: Yellow Group 4A. Innermost petals: Outer side: Yellow Group 4C. Inner Side: Yellow Group 4A.

*After opening, petals.*—Outermost petals: Outer side: Red-Purple Group 67D with light streaking of Red-Purple Group 65D at the middle zone. Inner Side: Red-Purple Group 62A. Innermost petals: Outer side: Red-Purple Group 67D with light streaking of Red-Purple Group 65D at the middle zone. Inner Side: Red-Purple Group 62A. After opening, basal petal spots: Outermost petals: Outer Side: Yellow Group 4C. Inner Side: Yellow Group 4C. Innermost petals: Outer Side: Yellow Group 4C. Inner Side: Yellow Group 4C.

General tonality: On open flower Red Group 52B. No change in the general tonality at the end of the $10^{th}$ day.

Petals:

*Petal Reflex.*—Variable. Slightly to strongly reflexed.

*Margin.*—Ruffled with strong undulations of margin observed.

*Shape.*—Apex: Round. Base: Acute.

*Size.*—40 mm (l)×46 mm (w).

*Texture.*—Smooth.

*Thickness.*—Average.

*Arrangement.*—Not Formal.

Petaloids:

*Quantity.*—5 to 10.

*Color.*—Upper surface is Red-Purple Group 73B. Lower Surface is Red-Purple Group 73A.

*Size.*—16 mm (l)×14 mm (w).

Reproductive organs:

*Pistils.*—Length: 12 mm. Quantity: 79.

*Pollen.*—None observed.

*Anthers.*—Color: Greyed-Orange Group 167B. Quantity: 101 (actual count).

*Filaments.*—Color: Yellow Group 3C. Length: 8 mm.

*Stigmas.*—Superior in location to the height of the anthers. Color: Yellow-Green Group 145D.

*Styles.*—Color: Yellow-Green Group 145D. Length: 10 to 12 mm.

*Hips.*—None Observed in the field nursery in Jackson County Oreg.

PLANT

Plant growth: Moderate, upright to bushy. When grown as a budded field grown plant on *Rosa multiflora* understock, the average height of the plant is 76 cm and the average width is 76 cm.

Stems:

*Color.*—Young wood: Yellow-Green Group 146D. Older wood: Yellow-Green Group 144A.

*Surface texture.*—Young wood: Smooth. Older wood: Rough.

Thorns:

*Incidence.*—2 thorns per 10 cm of stem.

*Size.*—Average length: 4 mm.

*Color.*—Mature and juvenile thorns are Greyed-Red Group 178A.

*Shape.*—Concave.

Plant foliage: Normal number of leaflets on normal leaves in middle of the stem: 7 leaflets.

*Compound leaf size.*—140 mm (l)×90 mm (w).

*Color.*—Mature Foliage: Upper surface is: Yellow-Green Group 146A. Lower surface is: Yellow-Green Group 146B. Juvenile foliage: Lower and upper surface: Yellow-Green Group 146A to 146 B with intonations of Greyed-Purple Group 183B. Lower surface is: Yellow-Green Group 146B.

Plant leaves and leaflets:

*Stipules.*—Size: 13 mm in length. Margins: Average quantity of stipitate glands. Color: Yellow-Green Group 144A.

*Petiole.*—Length: 15 to 20 mm. Diameter: 2 mm. Above: Color: Yellow-Green Group 1454B. Anthocyanin: Greyed-Red Group 182A. Underneath: Thorns present.

*Rachis.*—Above: Color: Yellow-Green Group 145B. Anthocyanin: Greyed-Red Group 182A. Underneath: Thorns present.

*Leaflet.*—Size: 50 mm (l)×30 mm (w). Edge: Serrated. Shape: Broadly ovate. Apex is cuspidate. Base is round. Texture: Rugose. Thickness: Thick. Arrangement: Odd pinnate. Venation: Reticulate. Glossiness: Very glossy.

Disease resistance: Above average resistance to mildew, rust, black spot, and *Botrytis* under normal growing conditions in Jackson County, Oreg.

Cold hardiness: The variety 'POULcs009' has been found to be cold tolerant to USDA Cold Hardiness Zone 6.

We claim:

1. A new and distinct variety of rose plant of the floribunda rose class, substantially as herein illustrated and described as a distinct and novel rose variety due to its abundant pink, disease resistance, and extended period of bloom.

* * * * *

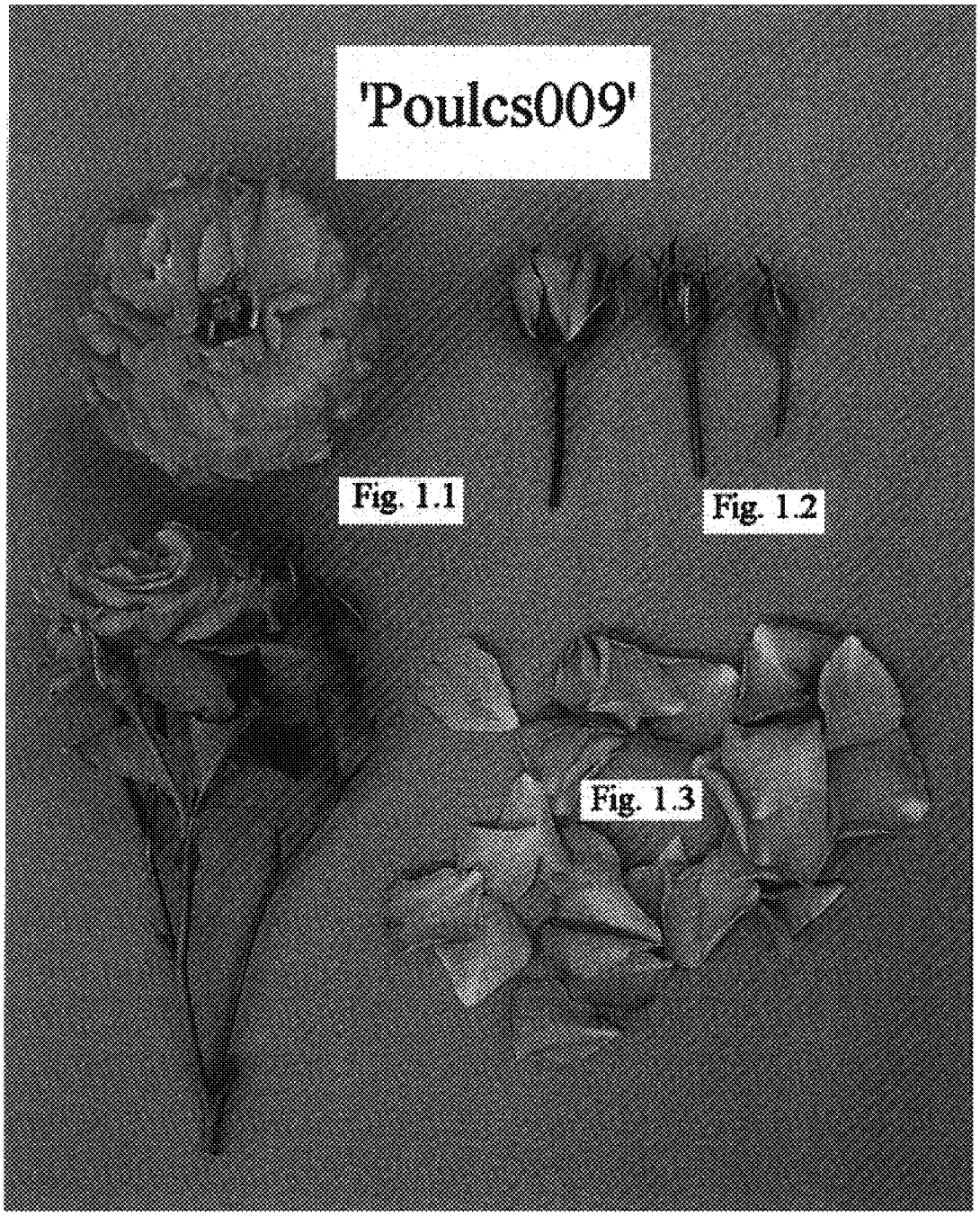
'Poulcs009'
Fig. 1.1
Fig. 1.2
Fig. 1.3

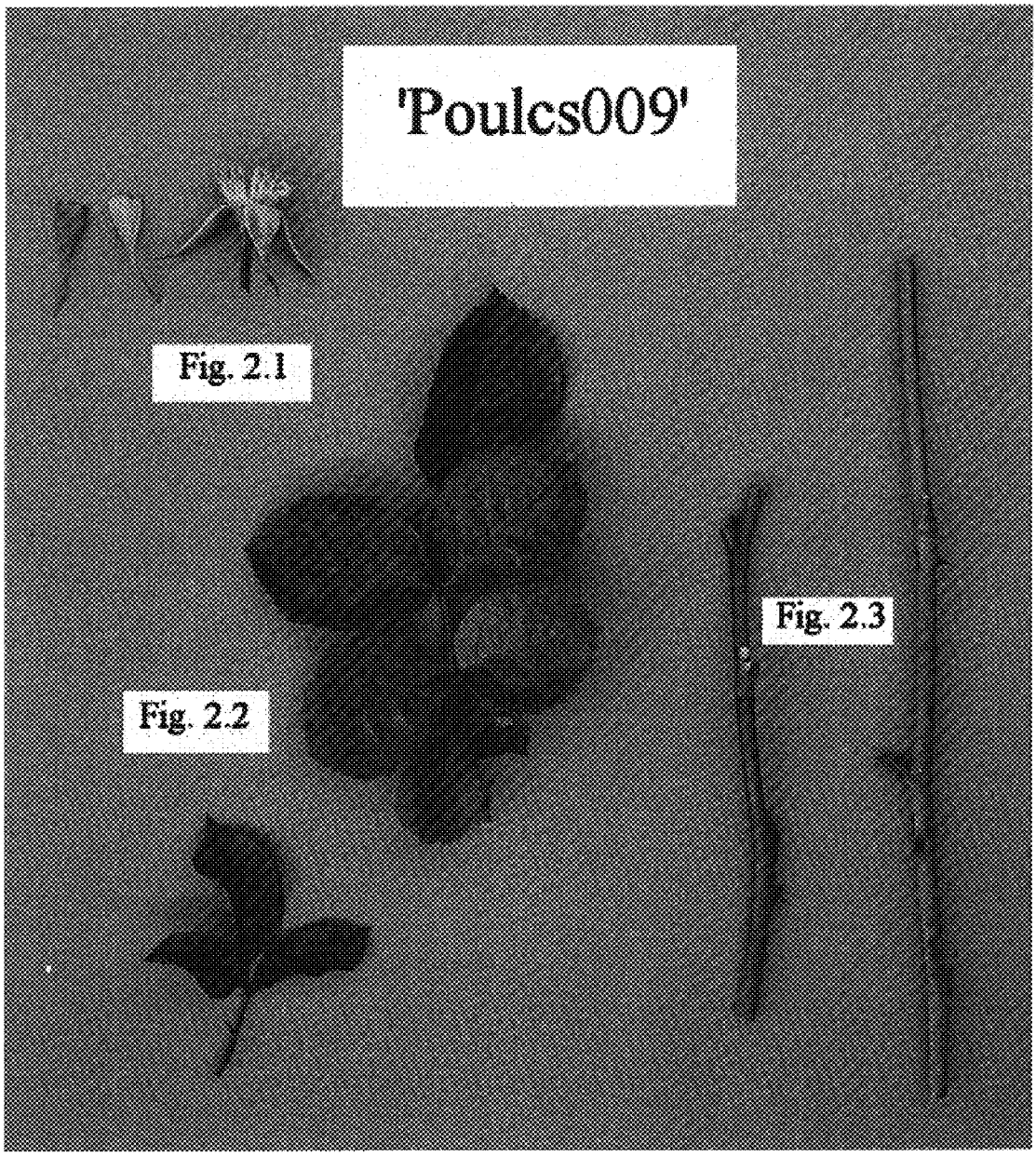
'Poulcs009'
Fig. 2.1
Fig. 2.2
Fig. 2.3